(12) United States Patent
Hwang et al.

(10) Patent No.: US 12,077,634 B2
(45) Date of Patent: Sep. 3, 2024

(54) METHOD FOR PURIFYING BIS-2-HYDROXYLETHYL TEREPHTHALATE AND POLYESTER RESIN COMPRISING SAME

(71) Applicant: SK CHEMICALS CO., LTD., Gyeonggi-do (KR)

(72) Inventors: Da-Young Hwang, Gyeonggi-do (KR); Kwang-Woo Park, Gyeonggi-do (KR); Yoo Jin Lee, Gyeonggi-do (KR); Jong-In Lee, Gyeonggi-do (KR)

(73) Assignee: SK Chemicals Co., Ltd., Gyeonggi-do (KR)

( * ) Notice: Subject to any disclaimer, the term of this patent is extended or adjusted under 35 U.S.C. 154(b) by 0 days.

(21) Appl. No.: 18/248,812

(22) PCT Filed: Sep. 14, 2021

(86) PCT No.: PCT/KR2021/012490
§ 371 (c)(1),
(2) Date: Apr. 12, 2023

(87) PCT Pub. No.: WO2022/108071
PCT Pub. Date: May 27, 2022

(65) Prior Publication Data
US 2023/0399462 A1    Dec. 14, 2023

(30) Foreign Application Priority Data
Nov. 18, 2020    (KR) .................... 10-2020-0154565

(51) Int. Cl.
*C08G 63/78* (2006.01)
*C07C 67/56* (2006.01)
*C08G 63/672* (2006.01)

(52) U.S. Cl.
CPC ............ *C08G 63/672* (2013.01); *C07C 67/56* (2013.01); *C08G 63/78* (2013.01)

(58) Field of Classification Search
USPC ...................................................... 528/298
See application file for complete search history.

(56) References Cited

U.S. PATENT DOCUMENTS

| | | | |
|---|---|---|---|
| 3,120,560 A | 2/1964 | Keck | |
| 3,268,575 A | 8/1966 | Keck | |
| 3,499,873 A * | 3/1970 | Franz | B01F 27/73 159/11.3 |
| 3,632,830 A | 1/1972 | Ichikawa et al. | |
| 4,211,858 A * | 7/1980 | Wada | C08F 2/005 528/272 |
| 9,127,136 B1 | 9/2015 | Bell et al. | |
| 2016/0060419 A1 | 3/2016 | Allen et al. | |
| 2020/0087450 A1 | 3/2020 | Lee et al. | |
| 2021/0380799 A1 | 12/2021 | Hwang et al. | |
| 2022/0119602 A1 | 4/2022 | Hwang et al. | |
| 2022/0380529 A1 | 12/2022 | Lee et al. | |

FOREIGN PATENT DOCUMENTS

| | | |
|---|---|---|
| CN | 109574835 | 4/2019 |
| EP | 0723951 | 7/1996 |
| JP | H10-45890 | 2/1998 |
| JP | 2000-053802 | 2/2000 |
| JP | 2000-169623 | 6/2000 |
| JP | 2002-121173 | 4/2002 |
| JP | 2004-123570 | 4/2004 |
| JP | 2004-189898 | 7/2004 |
| JP | 2005-089572 | 4/2005 |
| JP | 2006-070101 | 3/2006 |
| JP | 2008-088096 | 4/2008 |
| JP | 2016-536291 | 11/2016 |
| JP | 2020-521849 | 7/2020 |
| KR | 10-2012-0012930 | 2/2012 |
| KR | 10-2012-0078211 | 7/2012 |
| KR | 10-2020-0061948 | 6/2020 |
| WO | WO 2020/071708 | 4/2020 |
| WO | WO 2020/149469 | 7/2020 |

OTHER PUBLICATIONS

JP 2008088096 see machine translation (Year: 2008).*
JP 2009270083 A see machine translation (Year: 2009).*
International Search Report and Written Opinion for International (PCT) Patent Application No. PCT/KR2021/012490, dated Dec. 21, 2021, 8 pages.
English Translation of the International Search Report for International (PCT) Patent Application No. PCT/KR2021/012490, dated Dec. 21, 2021, 3 pages.

* cited by examiner

*Primary Examiner* — Terressa Boykin
(74) *Attorney, Agent, or Firm* — Sheridan Ross P.C.

(57) ABSTRACT

The present disclosure relates to a method for purifying bis-2-hydroxyethyl terephthalate with high purity and a polyester resin containing the same.

14 Claims, No Drawings

METHOD FOR PURIFYING BIS-2-HYDROXYLETHYL TEREPHTHALATE AND POLYESTER RESIN COMPRISING SAME

CROSS-REFERENCE TO RELATED APPLICATION

This application is a national stage application under 35 U.S.C. 371 and claims the benefit of PCT Application No. PCT/KR2021/012490 having an international filing date of 14 Sep. 2021, which designated the United States, and which PCT application claimed the benefit of Korean Patent Application No. 10-2020-0154565, filed on 18 Nov. 2020, the contents of each of which are incorporated herein by reference in their entireties.

TECHNICAL FIELD

The present disclosure relates to a method for purifying bis-2-hydroxyethyl terephthalate with high purity and a polyester resin containing the same.

BACKGROUND OF ART

Polyethylene terephthalate (PET) can be recycled after use, and the recycling methods are largely divided into physical recycling and chemical recycling. Physical recycling is to wash PET and then pulverize it into large particles or flakes for use, and chemical recycling is to recover monomers of PET by a chemical reaction. In the chemical recycling, PET is decomposed into monomers by a chemical reaction, and the produced monomers can be reused as raw materials for polyester production. The monomers produced by decomposition have the same chemical properties as the monomers used in the initial polymer synthesis.

PET can be prepared by condensation of terephthalic acid (TPA) with ethylene glycol (EG) or by reaction of dimethyl terephthalate (DMT) with EG. Both methods are about polymerization via bis(2-hydroxylethyl) terephthalate (BHET), a monomer of PET, to PET. In the recycling of PET, BHET, a monomer, can be obtained by depolymerizing PET with EG. BHET obtained from depolymerization can be used again for PET polymerization after separation and purification from by-products of depolymerization.

U.S. Pat. No. 9,127,136 attempted to separate and purify BHET by liquid chromatography using a mixed solvent of methanol and water. However, when the mixed solvent is used in the separation and purification process, there may be difficulties in the recovery process of the mixed solvent. In addition, U.S. Pat. Nos. 3,120,560 and 3,268,575 used water, ethylene dichloride, hexyl alcohol, and the like as a crystallization solvent for BHET purification. However, when ethylene dichloride is used as a solvent, crystallization occurs at a high temperature of 70° C. or higher, and separation at a high temperature is required. In addition, U.S. Pat. No. 3,632,830 attempted purification by BHET crystallization using an aromatic solvent such as benzene, toluene, and xylene. European Patent Publication No. EP0723951 attempted to purify BHET by crystallizing BHET obtained by filtration after depolymerization of PET.

Japanese Patent Publication No. 2000-169623 disclosed a BHET crystallization and purification process using ethylene glycol, but it is difficult to completely remove by-products, and low-quality polyester with color discoloration is produced from recycled polyester produced using the same. In addition, Japanese Patent Publication Nos. 2008-088096, 2000-053802, 2016-536291, etc. disclosed about the purification of BHET obtained by depolymerizing PET, but there is a problem in that the purified BHET and polyester to be produced using the same have unsatisfactory color quality.

Accordingly, the present inventors have conducted extensive research on a method for purifying bis-2-hydroxyethyl terephthalate that can dramatically improve the quality of bis-2-hydroxyethyl terephthalate recovered by chemical recycling of polyester. As a result, it was confirmed that when activated carbon was used in an aqueous solution of bis-2-hydroxyethyl terephthalate, the bis-2-hydroxyethyl terephthalate could be purified with high purity and also the color of the polyester to be prepared using the same could be improved, thereby completing the present invention.

DETAILED DESCRIPTION OF THE INVENTION

Technical Problem

In the present disclosure, there are provided a method for purifying bis-2-hydroxyethyl terephthalate with high purity and a polyester resin containing the same.

Technical Solution

In order to solve the above problems, there is provided a method for purifying bis-2-hydroxyethyl terephthalate, including the steps of:
 1) mixing bis-2-hydroxyethyl terephthalate and water;
 2) adding activated carbon to the mixture of step 1; and
 3) recovering bis-2-hydroxyethyl terephthalate from the mixture of step 2.

Hereinafter, the present invention will be described in detail for each step.

(Step 1)

The step 1 of the present disclosure is a step of mixing bis-2-hydroxyethyl terephthalate and water to prepare an aqueous solution of bis-2-hydroxyethyl terephthalate.

The bis-2-hydroxyethyl terephthalate to be purified in the present disclosure is not particularly limited, but bis-2-hydroxyethyl terephthalate obtained by depolymerization of polyester or polyester recovered after consumption is used.

In general, in the preparation of bis-2-hydroxyethyl terephthalate using recycled PET collected after consumption, PET is put into EG and depolymerized by boiling at a high temperature, but impurities such as dimers are generated along with bis-2-hydroxyethyl terephthalate. In addition, when EG is boiled at a high temperature in an oxygen-uncontrolled condition, it turns yellow and may come out with discolored chemicals. In addition, if recycled PET collected after consumption is colored, there may be an excess of pigments or dyes. During depolymerization, these dyes and pigments are dissolved in EG as they are, and if they are not properly purified, they may be mixed with the formed bis-2-hydroxyethyl terephthalate.

Therefore, in order to remove substances other than bis-2-hydroxyethyl terephthalate in the purification process as described above, the present disclosure is characterized in that an aqueous solution of bis-2-hydroxyethyl terephthalate is prepared, and then activated carbon is used as will be described later.

Preferably, bis-2-hydroxyethyl terephthalate and water are mixed in a weight ratio of 20:80 to 90:10 in step 1.

Preferably, a temperature of the water in step 1 is preferably 50 to 90° C.

This means a temperature of the aqueous solution of bis-2-hydroxyethyl terephthalate prepared in step 1, and the solubility of bis-2-hydroxyethyl terephthalate may be increased within the above temperature range. More preferably, the temperature of the water is 60 to 90° C.

(Step 2)

The step 2 of the present disclosure is a purification step of adding activated carbon to the aqueous solution of bis-2-hydroxyethyl terephthalate prepared in step 1. With this step, impurities in the aqueous solution of bis-2-hydroxyethyl terephthalate are adsorbed to the activated carbon, thereby removing the impurities.

Preferably, the activated carbon is added in an amount of 0.1 to 5.0 wt % based on a weight of the mixture of step 1.

Meanwhile, after the activated carbon is added, the aqueous solution of bis-2-hydroxyethyl terephthalate may be stirred in order to remove impurities with high efficiency. In addition, stirring time and stirring speed can be controlled by checking the degree of removal of impurities with the naked eye.

(Step 3)

The step 3 of the present disclosure is a step of recovering bis-2-hydroxyethyl terephthalate from the mixture of step 2.

The recovery is not particularly limited as long as the prepared bis-2-hydroxyethyl terephthalate is separated from the activated carbon, and may preferably be performed by filtration. Therefore, the step 3 may be performed by filtering the mixture of step 2 to recover a filtrate. Since the recovered filtrate contains purified bis-2-hydroxyethyl terephthalate, the recovered filtrate can be used for the preparation of a polyester copolymer to be described later without a separate additional process.

In addition, in order to further purify bis-2-hydroxyethyl terephthalate, bis-2-hydroxyethyl terephthalate crystals may be induced from the recovered filtrate and the resulting crystals may be recovered.

Specifically, the filtrate may be cooled to 10 to 40° C. to recover bis-2-hydroxyethyl terephthalate crystals. The produced crystals may be recovered by separating the resulting bis-2-hydroxyethyl terephthalate crystals and solution, preferably by centrifugation.

(Preparation of Polyester Copolymer)

Since the bis-2-hydroxyethyl terephthalate purified by the above-described purification method has high purity by removing impurities, it can be used in the preparation of a polyester copolymer.

Specifically, there is provided the following method for preparation of a polyester copolymer including the steps of:
1) preparing an oligomer by an esterification reaction of an aqueous solution containing bis-2-hydroxyethyl terephthalate purified by the above-described purification method according to the present disclosure, a dicarboxylic acid or its derivative, and a diol containing ethylene glycol and a comonomer (step 1); and
2) preparing a polyester copolymer by a polycondensation reaction of the oligomer (step 2),
wherein a concentration of the aqueous solution containing bis-2-hydroxyethyl terephthalate is 25 to 99 wt %.

The step 1 of the method for preparation of a polyester copolymer is a step of preparing an oligomer by an esterification reaction of an aqueous solution containing bis-2-hydroxyethyl terephthalate, a dicarboxylic acid or its derivative, and a diol containing ethylene glycol and a comonomer.

The aqueous solution of bis-2-hydroxyethyl terephthalate may be an aqueous solution of bis-2-hydroxyethyl terephthalate purified by the above-described purification method according to the present disclosure, or an aqueous solution in which bis-2-hydroxyethyl terephthalate crystals purified by the purification method according to the present disclosure are dissolved in water.

Preferably, the concentration of the aqueous solution containing bis-2-hydroxyethyl terephthalate may be 25 to 99 wt %. When the concentration is less than 25 wt %, the reaction efficiency is lowered due to the low concentration of bis-2-hydroxyethyl terephthalate. When the concentration exceeds 99 wt %, it is difficult to induce a uniform esterification reaction due to the high concentration of bis-2-hydroxyethyl terephthalate.

In addition, a temperature of the aqueous solution containing bis-2-hydroxyethyl terephthalate may preferably be 25 to 100° C., and more preferably 30 to 90° C.

Meanwhile, the dicarboxylic acid or its derivative used in the present disclosure refers to a main monomer constituting the polyester copolymer together with the diol component. In particular, the dicarboxylic acid includes terephthalic acid, and physical properties such as heat resistance, chemical resistance, and weather resistance of the polyester copolymer according to the present disclosure may be improved by terephthalic acid. In addition, the terephthalic acid derivative may be terephthalic acid alkyl ester, preferably dimethylterephthalic acid.

The dicarboxylic acid may further include an aromatic dicarboxylic acid, an aliphatic dicarboxylic acid, or a mixture thereof in addition to terephthalic acid.

In this case, the dicarboxylic acid other than terephthalic acid is preferably included in 1 to 30 wt % based on a total weight of the total dicarboxylic acid component.

The aromatic dicarboxylic acid component may be an aromatic dicarboxylic acid having 8 to 20 carbon atoms, preferably 8 to 14 carbon atoms, or a mixture thereof. Specific examples of the aromatic dicarboxylic acid include isophthalic acid, naphthalenedicarboxylic acid such as 2,6-naphthalenedicarboxylic acid, diphenyl dicarboxylic acid, 4,4'-stilbenedicarboxylic acid, 2,5-furandicarboxylic acid, 2,5-thiophenedicarboxylic acid, and the like, but are not limited thereto. The aliphatic dicarboxylic acid component may be an aliphatic dicarboxylic acid component having 4 to 20 carbon atoms, preferably 4 to 12 carbon atoms, or a mixture thereof. Specific examples of the aliphatic dicarboxylic acid include linear, branched or cyclic aliphatic dicarboxylic acid components including cyclohexanedicarboxylic acid such as 1,4-cyclohexanedicarboxylic acid and 1,3-cyclohexanedicarboxylic acid, phthalic acid, sebacic acid, succinic acid, isodecylsuccinic acid, maleic acid, fumaric acid, adipic acid, glutaric acid, and azelaic acid, but are not limited thereto.

The diol component used in the present disclosure refers to a main monomer constituting the polyester copolymer together with the above-described dicarboxylic acid or its derivative. In particular, the diol component contains ethylene glycol and a comonomer, and the comonomer includes cyclohexanedimethanol, isosorbide, or diethylene glycol.

The ethylene glycol is a component that contributes to improving transparency and impact strength of the polyester copolymer. Preferably, the ethylene glycol may be used in an amount of 5 to 100 moles based on 100 moles of the total diol component.

The cyclohexanedimethanol (e.g., 1,2-cyclohexanedimethanol, 1,3-cyclohexanedimethanol or 1,4-cyclohexanedimethanol) is a component that contributes to improving transparency and impact strength of the polyester copolymer to be prepared. Preferably, the cyclohexanedimethanol may be used in an amount of 5 to 90 moles based on 100 moles of the residue of the total diol component.

The isosorbide is used to improve processability of the polyester copolymer to be prepared. Although the diol of cyclohexanedimethanol and ethylene glycol improves the transparency and impact resistance of the polyester copolymer, shear thinning characteristics should be improved and a crystallization rate should be lowered for improving processability. However, it is difficult to achieve these effects using only the cyclohexanedimethanol and ethylene glycol. When containing isosorbide as the diol component, the shear thinning characteristics are improved and the crystallization rate is lowered while the transparency and impact strength are maintained, thereby improving the processability of the polyester copolymer to be prepared. Preferably, the isosorbide may be used in an amount of 0.1 to 50 moles based on 100 moles of the total diol component.

Meanwhile, as will be described later, the polyester copolymer prepared according to the present disclosure includes 1 to 90 wt % of the residue of bis-2-hydroxyethyl terephthalate. To this end, the concentration of the recycled bis-2-hydroxyethyl terephthalate solution prepared in step 1 is adjusted as described above. When the residue of the recycled bis-2-hydroxyethyl terephthalate is less than 1 wt %, the content of the above-mentioned diol is relatively high, and accordingly, more by-products derived from the diol component, especially by-products derived from ethylene glycol, are generated, resulting in deterioration of the quality of the polyester copolymer. In addition, when the residue of the recycled bis-2-hydroxyethyl terephthalate is more than 90 wt %, there is a problem in that the color quality and transparency of the polyester copolymer are deteriorated.

The esterification reaction may be performed at a pressure of 0.1 to 3.0 kg/cm$^2$ and a temperature of 200 to 300° C. The conditions of the esterification reaction may be appropriately adjusted according to specific characteristics of the polyester to be prepared, the ratio of each component, or process conditions. Specifically, the temperature of the esterification reaction may be 240 to 295° C., more preferably 245 to 275° C.

The esterification reaction may be performed in a batch or continuous manner. The respective raw materials may be separately added, or they are added in the form of a slurry by mixing the diol component with the dicarboxylic acid component and recycled bis-2-hydroxyethyl terephthalate solution. In addition, a diol component such as isosorbide, which is a solid component at room temperature, may be dissolved in water or ethylene glycol, and then mixed with a dicarboxylic acid component such as terephthalic acid to form a slurry. Alternatively, after the isosorbide is melted at 60° C. or higher, a slurry may be prepared by mixing a dicarboxylic acid component such as terephthalic acid and other diol components. In addition, water may be added to the mixed slurry to help increase fluidity of the slurry.

Preferably, the esterification reaction of step 2 is performed for 2 hours to 10 hours. The reaction time affects quality of the finally prepared polyester copolymer, and when the reaction time is less than 2 hours or more than 10 hours, color quality of the finally prepared polyester copolymer is deteriorated.

Meanwhile, the esterification reaction may use a catalyst including a titanium-based compound, a germanium-based compound, an antimony-based compound, an aluminum-based compound, a tin-based compound, or a mixture thereof.

Examples of the titanium-based compound may include tetraethyl titanate, acetyltripropyl titanate, tetrapropyl titanate, tetrabutyl titanate, 2-ethylhexyl titanate, octylene glycol titanate, lactate titanate, triethanolamine titanate, acetylacetonate titanate, ethylacetoacetic ester titanate, isostearyl titanate, titanium dioxide, and the like. Examples of the germanium-based compound may include germanium dioxide, germanium tetrachloride, germanium ethyleneglycoxide, germanium acetate, a copolymer thereof, and a mixture thereof. Preferably, germanium dioxide may be used, and the germanium dioxide may be in a crystalline or amorphous form. Glycol soluble germanium dioxide may be also used.

The step 2 of the method for preparation of a polyester copolymer is a step of preparing a polyester copolymer by a polycondensation reaction of the oligomer.

The polycondensation reaction may be performed by reacting the esterification product at a temperature of 240 to 300° C. and a pressure of 400 to 0.01 mmHg. In addition, the polycondensation reaction may be performed for 1 to 10 hours.

The temperature and pressure conditions of the polycondensation reaction enable the removal of glycol, which is a by-product of the polycondensation reaction, from the system. In addition, when the polycondensation reaction is performed within the reaction time above, the intrinsic viscosity of the final product may reach an appropriate level.

In addition, there is provided a polyester copolymer prepared according to the method for preparation of a polyester copolymer described above.

Meanwhile, the polyester copolymer according to the present disclosure may have an intrinsic viscosity of 0.50 to 1.0 dl/g, preferably 0.50 to 0.85 dl/g, and more preferably 0.55 to 0.80 dl/g. The method for measuring the intrinsic viscosity will be specified in Examples to be described later.

In addition, '(Hunter L value)–(Hunter b value)' (hereinafter, referred to as Plaque Color L-b) measured with respect to a 6 mm-thick specimen of the polyester copolymer according to the present disclosure may be 87 or more, and more preferably 88 or more, 89 or more, or 90 or more. In addition, the upper limit of the Plaque Color L-b may be 100, and in the present disclosure, the Plaque Color L-b may be 99 or less, 98 or less, 97 or less, 96 or less, or 95 or less. The method for measuring the Plaque Color L-b will be specified in Examples to be described later.

In addition, a haze measured with respect to a 6 mm-thick specimen of the polyester copolymer according to the present disclosure may be 3 or less, and more preferably 2.5 or less. In addition, the upper limit of the haze may be 0, and in the present disclosure, the haze may be 0.1 or more, 0.2 or more, 0.3 or more, 0.4 or more, or 0.5 or more. The method for measuring the haze will be specified in Examples to be described later.

In the present disclosure, there is also provided a product including the polyester copolymer.

Advantageous Effects

As described above, the purification method according to the present disclosure can purify bis-2-hydroxyethyl terephthalate with high purity, and using the bis-2-hydroxyethyl terephthalate as a polyester copolymer allows good color quality.

DETAILED DESCRIPTION OF THE EMBODIMENTS

Hereinafter, preferred examples are presented to help the understanding of the present invention. However, the following examples are provided only for easier understanding of the present invention, and the present invention is not limited thereto.

Bis-2-hydroxyethyl terephthalate (BHET) with commercially available quality was used, and the same was used in the following Preparation Examples, Examples, and Comparative Examples.

PREPARATION EXAMPLES

Preparation Example 1: BHET Purification Using Distilled Water and Activated Carbon 1250 g of distilled water was added to a 20 L vessel, and then heated with stirring at 70° C. When the temperature reached 70° C., 250 g of BHET was added and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter. BHET aqueous solution passed through the filter was cooled to room temperature (23° C.) to obtain crystalline BHET, separated from the mixed solution through a filter, and dried under reduced pressure to finally obtain purified BHET.

Preparation Example 2: BHET Purification Using Activated Carbon and Used in Polymerization Process in Aqueous Solution State 300 g of distilled water was added to a 3 L vessel, and then heated with stirring at 85° C. When the temperature reached 85° C., 2000 g of BHET was added slowly and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter.

Comparative Preparation Example 1: BHET Purification Using Distilled Water

BHET was obtained in the same manner as in Preparation Example 1, except that adsorption purification using activated carbon was not performed in Preparation Example 1.

Comparative Preparation Example 2: Unpurified BHET Aqueous Solution

An aqueous solution of BHET dissolved in the same composition as in Preparation Example 2 was prepared without separate purification.

Comparative Preparation Example 3: Unpurified BHET

BHET crystals that were not separately purified and mixed with distilled water were prepared.

The purity, color, and yield of BHET obtained in Preparation Examples and Comparative Preparation Examples were measured and shown in Table 1 below. At this time, the color was measured for each crystal, and was measured with a spectrophotometer (CM-3600A) from Konica Minolta.

TABLE 1

|  | Prep. Ex. 1 | Prep. Ex.2 | Comp. Prep. Ex. 1 | Comp. Prep. Ex. 2 | Comp. Prep. Ex. 3 |
| --- | --- | --- | --- | --- | --- |
| Treatment method | adsorption/crystallization | adsorption | distilled water crystallization | unpurified aqueous solution | unpurified raw material |
| LC purity % | 97.7% | 97.0% | 97.6% | 96.9% | 96.9% |
| Color L-b | 97.9 | (unmeasured) | 96.5 | (unmeasured) | 95.2 |
| Yield | 93.7% | 98.9% | 93.8% | — | — |

EXAMPLES

Example 1

200 g of distilled water was added to a 3 L vessel, and then heated with stirring at 85° C. When the temperature reached 85° C., 1269.7 g of BHET was added slowly and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter to prepare a BHET solution (concentration: 86.4%).

The above-prepared BHET solution, TPA (terephthalic acid; 2361.8 g), EG (ethylene glycol; 673.5 g), CHDM (1,4-cyclohexanedimethanol; 221.5 g), and ISB (isosorbide; 98.2 g) were placed in a 10 L reactor to which a column, and a condenser capable of being cooled by water were connected, and $GeO_2$ (1.0 g) as a catalyst, phosphoric acid (1.46 g) as a stabilizer, and cobalt acetate (0.7 g) as a coloring agent were added thereto.

Then, nitrogen was injected into the reactor to form a pressurized state in which the pressure of the reactor was higher than normal pressure by 1.0 kgf/cm² (absolute pressure: 1495.6 mmHg). Then, the temperature of the reactor was raised to 220° C. over 90 minutes, maintained at 220° C. for 2 hours, and then raised to 260° C. over 2 hours. Thereafter, an esterification reaction proceeded for 245 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.55 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 200° C. at a rate of 40° C./hour, and maintained at 200° C. The solid-phase polymerization reaction was performed until the intrinsic viscosity (IV) of the particles in the reactor reached 0.70 dl/g to prepare a polyester copolymer.

Example 2

An aqueous solution of r-BHET was prepared by dissolving r-BHET (3461.1 g) prepared in Preparation Example 1 in water (200 g) at 70° C.

The above-prepared aqueous solution of r-BHET, TPA (969.4 g), EG (12.1 g), CHDM (140.2 g), and ISB (113.7 g) were placed in a 10 L reactor to which a column, and a condenser capable of being cooled by water were connected, and $GeO_2$ (1.0 g) as a catalyst, phosphoric acid (1.46 g) as a stabilizer, and cobalt acetate (0.7 g) as a coloring agent were added thereto.

Then, nitrogen was injected into the reactor to form a pressurized state in which the pressure of the reactor was higher than normal pressure by 1.0 $kgf/cm^2$ (absolute pressure: 1495.6 mmHg). Then, the temperature of the reactor was raised to 220° C. over 90 minutes, maintained at 220° C. for 2 hours, and then raised to 260° C. over 2 hours. Thereafter, an esterification reaction proceeded for 200 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 200° C. at a rate of 40° C./hour, and maintained at 200° C. The solid-phase polymerization reaction was performed until the intrinsic viscosity (IV) of the particles in the reactor reached 0.95 dl/g to prepare a polyester copolymer.

Example 3

200 g of distilled water was added to a 3 L vessel, and then heated with stirring at 85° C. When the temperature reached 85° C., 3461.1 g of BHET was added slowly and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter to prepare a BHET solution (concentration: 94.5%).

The above-prepared BHET solution, TPA (420.3 g), EG (39.2 g), and CHDM (121.5 g) were placed in a 10 L reactor to which a column, and a condenser capable of being cooled by water were connected, and $TiO_2/SiO_2$ copolymer (0.5 g) as a catalyst, phosphoric acid (1.46 g) as a stabilizer, Polysynthren Blue RLS (manufactured by Clarient, 0.016 g) as a blue toner, and Solvaperm Red BB (manufactured by Clarient, 0.004 g) as a red toner were added thereto.

Then, nitrogen was injected into the reactor to form a pressurized state in which the pressure of the reactor was higher than normal pressure by 0.5 $kgf/cm^2$ (absolute pressure: 1127.8 mmHg). Then, the temperature of the reactor was raised to 220° C. over 90 minutes, maintained at 220° C. for 2 hours, and then raised to 260° C. over 2 hours. Thereafter, an esterification reaction proceeded for 500 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 275° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 210° C. at a rate of 40° C./hour, and maintained at 210° C. The solid-phase polymerization reaction was performed until the intrinsic viscosity (IV) of the particles in the reactor reached 0.80 dl/g to prepare a polyester copolymer.

Example 4

The r-BHET (795.8 g) prepared in Preparation Example 1, TPA (3814.0 g), EG (1554.0 g), and CHDM (188.0 g) were placed in a 10 L reactor to which a column, and a condenser capable of being cooled by water were connected, and $TiO_2/SiO_2$ copolymer (0.5 g) as a catalyst, phosphoric acid (1.46 g) as a stabilizer, and cobalt acetate (1.1 g) as a coloring agent were added thereto.

Then, nitrogen was injected into the reactor to form a pressurized state in which the pressure of the reactor was higher than normal pressure by 1.0 kgf/cm$^2$ (absolute pressure: 1495.6 mmHg). Then, the temperature of the reactor was raised to 220° C. over 90 minutes, maintained at 220° C. for 2 hours, and then raised to 250° C. over 2 hours. Thereafter, an esterification reaction proceeded for 500 minutes until the mixture in the reactor became transparent with the naked eye while maintaining the temperature of the reactor at 250° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 265° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.55 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 220° C. at a rate of 40° C./hour, and maintained at 220° C. The solid-phase polymerization reaction was performed until the intrinsic viscosity (IV) of the particles in the reactor reached 0.85 dl/g to prepare a polyester copolymer.

Example 5

300 g of distilled water was added to a 3 L vessel, and then heated with stirring at 85° C. When the temperature reached 85° C., 2439.2 g of BHET was added slowly and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter to prepare a BHET solution (concentration: 89.0%).

The above-prepared BHET solution, TPA (1471.5 g), EG (68.7 g), and CHDM (797.8 g) were placed in a 10 L reactor to which a column, and a condenser capable of being cooled by water were connected, and $TiO_2/SiO_2$ copolymer (1.0 g) as a catalyst, phosphoric acid (1.46 g) as a stabilizer, and cobalt acetate (0.8 g) as a coloring agent were added thereto.

Then, nitrogen was injected into the reactor to form a pressurized state in which the pressure of the reactor was higher than normal pressure by 2.0 kgf/cm$^2$ (absolute pressure: 2231.1 mmHg). Then, the temperature of the reactor was raised to 220° C. over 90 minutes, maintained at 220° C. for 2 hours, and then raised to 255° C. over 2 hours. Thereafter, an esterification reaction proceeded for 360 minutes until the mixture in the reactor became transparent with the naked eye while maintaining the temperature of the reactor at 255° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 285° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.70 dl/g. When the intrinsic viscosity of the mixture in the reactor reached a desired level, the mixture was discharged out of the reactor and stranded. This was solidified with a cooling liquid and granulated to have an average weight of about 12 to 14 mg to prepare a polyester copolymer.

Example 6

The above prepared r-BHET (40.9 g), TPA (2643.1 g), EG (329.1 g), CHDM (1158.0 g), and ISB (587.0 g) were placed in a 10 L reactor to which a column, and a condenser capable of being cooled by water were connected, and $GeO_2$ (1.0 g) as a catalyst, phosphoric acid (1.46 g) as a stabilizer, Polysynthren Blue RLS (manufactured by Clarient, 0.020 g) as a blue toner, and Solvaperm Red BB (manufactured by Clarient, 0.008 g) as a red toner were added thereto.

Then, nitrogen was injected into the reactor to form a pressurized state in which the pressure of the reactor was higher than normal pressure by 0.5 kgf/cm² (absolute pressure: 1127.8 mmHg). Then, the temperature of the reactor was raised to 220° C. over 90 minutes, maintained at 220° C. for 2 hours, and then raised to 260° C. over 2 hours. Thereafter, an esterification reaction proceeded for 360 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 275° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.80 dl/g. When the intrinsic viscosity of the mixture in the reactor reached a desired level, the mixture was discharged out of the reactor and stranded. This was solidified with a cooling liquid and granulated to have an average weight of about 12 to 14 mg to prepare a polyester copolymer.

Example 7

100 g of distilled water was added to a 3 L vessel, and then heated with stirring at 85° C. When the temperature reached 85° C., 3418.5 g of BHET was added slowly and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter to prepare a BHET solution (concentration: 97.2%).

The above-prepared r-BHET solution, TPA (957.5 g), DMT (dimethyl terephthalate; 1119.0 g), EG (345.7 g), CHDM (221.5 g), and ISB (84.2 g) were placed in a 10 L reactor to which a column, and a condenser capable of being cooled by water were connected, and Mn(II) acetate tetrahydrate (1.5 g) and $Sb_2O_3$ (1.8 g) as a catalyst, and cobalt acetate (0.7 g) as a coloring agent were added thereto.

Then, nitrogen was injected into the reactor to bring the pressure of the reactor to normal pressure. Then, the temperature of the reactor was raised to 220° C. over 90 minutes, maintained at 220° C. for 2 hours, and then raised to 240° C. over 2 hours. Thereafter, an esterification reaction proceeded for 150 minutes until the mixture in the reactor became transparent with the naked eye while maintaining the temperature of the reactor at 240° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 265° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 200° C. at a rate of 40° C./hour, and maintained at 200° C. The solid-phase polymerization reaction was performed until the intrinsic viscosity (IV) of the particles in the reactor reached 0.95 dl/g to prepare a polyester copolymer.

Example 8

An aqueous solution of r-BHET was prepared by dissolving r-BHET (3461.1 g) prepared in Preparation Example 1 in water (1500 g) at 95° C.

The above-prepared aqueous solution of r-BHET, TPA (969.4 g), IPA (isophthalic acid; 2262.0 g), EG (12.1 g), CHDM (140.2 g), and ISB (113.7 g) were placed in a 10 L reactor to which a column, and a condenser capable of being cooled by water were connected, and $GeO_2$ (1.0 g) as a catalyst, and cobalt acetate (0.7 g) as a coloring agent were added thereto.

Then, nitrogen was injected into the reactor to form a pressurized state in which the pressure of the reactor was higher than normal pressure by 3.0 kgf/cm² (absolute pressure: 2956.7 mmHg). Then, the temperature of the reactor was raised to 220° C. over 90 minutes, maintained at 220° C. for 2 hours, and then raised to 260° C. over 2 hours. Thereafter, an esterification reaction proceeded for 200 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the 7 L reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 190° C. at a rate of 40° C./hour, and maintained at 190° C. The solid-phase polymerization reaction was performed until the intrinsic viscosity (IV) of the particles in the reactor reached 1.0 dl/g to prepare a polyester copolymer.

Comparative Example 1

The r-BHET (1291.0 g) of Comparative Preparation Example 3, TPA (2401.4 g), EG (721.2 g), CHDM (140.8 g), and ISB (99.9 g) were placed in a 10 L reactor to which a column, and a condenser capable of being cooled by water were connected, and $GeO_2$ (1.0 g) as a catalyst and phosphoric acid (1.46 g) as a stabilizer were added thereto.

Then, nitrogen was injected into the reactor to form a pressurized state in which the pressure of the reactor was higher than normal pressure by 0.5 kgf/cm$^2$ (absolute pressure: 1127.8 mmHg). Then, the temperature of the reactor was raised to 220° C. over 90 minutes, maintained at 220° C. for 2 hours, and then raised to 260° C. over 2 hours. Thereafter, an esterification reaction proceeded for 720 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 200° C. at a rate of 40° C./hour, and maintained at 200° C. The solid-phase polymerization reaction was performed until the intrinsic viscosity (IV) of the particles in the reactor reached 0.70 dl/g to prepare a polyester copolymer.

Comparative Example 2

The r-BHET (304.1 g) prepared in Comparative Preparation Example 1, TPA (2640.8 g), EG (583.3 g), CHDM (1231.6 g), and ISB (25.0 g) were placed in a 10 L reactor to which a column, and a condenser capable of being cooled by water were connected, and $GeO_2$ (1.0 g) as a catalyst, phosphoric acid (1.46 g) as a stabilizer, Polysynthren Blue RLS (manufactured by Clarient, 0.012 g) as a blue toner, and Solvaperm Red BB (manufactured by Clarient, 0.004 g) as a red toner were added thereto.

Then, nitrogen was injected into the reactor to form a pressurized state in which the pressure of the reactor was higher than normal pressure by 0.5 kgf/cm$^2$ (absolute pressure: 1127.8 mmHg). Then, the temperature of the reactor was raised to 220° C. over 90 minutes, maintained at 220° C. for 2 hours, and then raised to 255° C. over 2 hours. Thereafter, an esterification reaction proceeded for 750 minutes until the mixture in the reactor became transparent with the naked eye while maintaining the temperature of the reactor at 255° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.75 dl/g. When the intrinsic viscosity of the mixture in the reactor reached a desired level, the mixture was discharged out of the reactor and stranded. This was solidified with a cooling liquid and granulated to have an average weight of about 12 to 14 mg to prepare a polyester copolymer.

Comparative Example 3

The r-BHET (3898.7 g) prepared in Preparation Example 1, TPA (162.6 g), EG (81.0 g), and ISB (95.4 g) were placed in a 10 L reactor to which a column, and a condenser capable of being cooled by water were connected, and Ge$_2$O (1.0 g) as a catalyst, phosphoric acid (1.46 g) as a stabilizer, Polysynthren Blue RLS (manufactured by Clarient, 0.010 g) as a blue toner, and Solvaperm Red BB (manufactured by Clarient, 0.003 g) as a red toner were added thereto.

Then, nitrogen was injected into the reactor to form a pressurized state in which the pressure of the reactor was higher than normal pressure by 0.1 kgf/cm$^2$ (absolute pressure: 823.6 mmHg). Then, the temperature of the reactor was raised to 220° C. over 90 minutes, maintained at 220° C. for 2 hours, and then raised to 260° C. over 2 hours. Thereafter, an esterification reaction proceeded for 850 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 270° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.65 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 220° C. at a rate of 40° C./hour, and maintained at 220° C. The solid-phase polymerization reaction was performed until the intrinsic viscosity (IV) of the particles in the reactor reached 0.85 dl/g to prepare a polyester copolymer.

Comparative Example 4

2300 g of distilled water was added to a 3 L vessel, and then heated with stirring at 85° C. When the temperature reached 85° C., 735.6 g of BHET was added slowly and completely dissolved to prepare a BHET solution (concentration: 24.2%).

The above-prepared BHET solution, TPA (2724.3 g), EG (1239.0 g), CHDM (222.4 g), and ISB (98.7 g) were placed in a 10 L reactor to which a column, and a condenser capable of being cooled by water were connected, and Ge$_2$O (1.0 g) as a catalyst, and phosphoric acid (1.46 g) as a stabilizer were added thereto.

Then, nitrogen was injected into the reactor to form a pressurized state in which the pressure of the reactor was higher than normal pressure by 0.5 kgf/cm$^2$ (absolute pressure: 1127.8 mmHg). Then, the temperature of the reactor was raised to 220° C. over 90 minutes, maintained at 220° C. for 2 hours, and then raised to 260° C. over 2 hours. Thereafter, an esterification reaction proceeded for 650 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg.

The particles were allowed to stand at 150° C. for 1 hour to crystallize, and then put into a 20 L solid-phase polymerization reactor. Then, nitrogen was flowed into the reactor at a rate of 50 L/min. Herein, the temperature of the reactor was raised from room temperature to 140° C. at a rate of 40° C./hour, and maintained at 140° C. for 3 hours. Thereafter, the temperature was further raised to 200° C. at a rate of 40° C./hour, and maintained at 200° C. The solid-phase polymerization reaction was performed until the intrinsic viscosity (IV) of the particles in the reactor reached 0.70 dl/g to prepare a polyester copolymer.

Comparative Example 5

3000 g of distilled water was added to a 3 L vessel, and then heated with stirring at 85° C. When the temperature reached 85° C., 615.7 g of BHET was added slowly and completely dissolved. When BHET was completely dissolved, 0.5 wt % of powdered activated carbon based on the added BHET was added, followed by stirring for 1 hour to adsorb impurities. Thereafter, undissolved impurities and activated carbon were removed through a heated filter to prepare a BHET solution (concentration: 17.0%).

The above-prepared BHET solution, TPA (2280.0 g), EG (566.0 g), CHDM (698.1 g), and ISB (82.6 g) were placed in a 10 L reactor to which a column, and a condenser capable of being cooled by water were connected, and Ge$_2$O (1.0 g) as a catalyst, phosphoric acid (1.46 g) as a stabilizer, and cobalt acetate (0.7 g) as a coloring agent were added thereto.

Then, nitrogen was injected into the reactor to form a pressurized state in which the pressure of the reactor was higher than normal pressure by 0.5 kgf/cm$^2$ (absolute pressure: 1127.8 mmHg). Then, the temperature of the reactor was raised to 220° C. over 90 minutes, maintained at 220° C. for 2 hours, and then raised to 260° C. over 2 hours. Thereafter, an esterification reaction proceeded for 900 minutes until the mixture in the reactor became transparent with the naked eye while maintaining the temperature of the reactor at 260° C. In this process, by-products flowed through the column and condenser. When the esterification reaction was completed, the nitrogen in the pressurized reactor was discharged to the outside to lower the pressure of the reactor to normal pressure, and then the mixture in the reactor was transferred to a 7 L reactor capable of vacuum reaction.

Then, the pressure of the reactor was reduced from normal pressure to 5 Torr (absolute pressure: 5 mmHg) over 30 minutes, and the temperature of the reactor was raised to 280° C. over 1 hour to proceed a polycondensation reaction while maintaining the pressure of the reactor at 1 Torr (absolute pressure: 1 mmHg) or less. In the initial stage of the polycondensation reaction, a stirring rate was set high, but when the stirring force is weakened due to an increase in the viscosity of the reactant as the polycondensation reaction progresses or the temperature of the reactant rises above the set temperature, the stirring rate may be appropriately adjusted. The polycondensation reaction was performed until an intrinsic viscosity (IV) of the mixture (melt) in the reactor became 0.60 dl/g. When the intrinsic viscosity of the mixture in the reactor reached a desired level, the mixture was discharged out of the reactor and stranded. This was solidified with a cooling liquid and granulated to have an average weight of about 12 to 14 mg to prepare a polyester copolymer.

EXPERIMENTAL EXAMPLES

Physical properties of the polyester copolymers prepared in Examples and Comparative Examples were evaluated as follows.

1) Residue Composition

The residue composition (mol %) derived from acid and diol in the polyester resin was confirmed through 1H-NMR spectrum obtained at 25° C. using a nuclear magnetic resonance apparatus (JEOL, 600 MHz FT-NMR) after dissolving the sample in a CDCl$_3$ solvent at a concentration of 3 mg/mL. In addition, the residue of TMA was confirmed by quantitative analysis of spectrum in which the content of benzene-1,2,4-triethylcarboxylate produced by the reaction of ethanol with TMA through ethanolysis was measured at 250° C. using gas chromatography (Agilent Technologies, 7890B). And, it was confirmed as the content (wt %) based on a total weight of the polyester resin.

2) Intrinsic Viscosity

After dissolving the polyester copolymer in orthochlorophenol (OCP) at a concentration of 0.12% at 150° C., the intrinsic viscosity was measured in a constant temperature bath at 35° C. using an Ubbelohde viscometer. Specifically, a temperature of the viscometer was maintained at 35° C., and the time taken (efflux time; to) for a solvent to pass between certain internal sections of the viscometer and the time taken (t) for a solution to pass the viscometer were measured. Subsequently, a specific viscosity was calculated by substituting to and t into Formula 1, and the intrinsic viscosity was calculated by substituting the calculated specific viscosity into Formula 2.

$$\eta_{sp} = \frac{t - t_0}{t_0} \quad \text{[Formula 1]}$$

$$[\eta] = \frac{\sqrt{1 + 4A\eta_{sp}} - 1}{2Ac} \quad \text{[Formula 2]}$$

3) Plaque Color L-b

The chromaticity and brightness of the sample were measured using Varian Cary 5 UV/Vis/NIR spectrophotometer equipped with a diffuse reflection accessory. A polyester resin specimen having a thickness of 6 mm was prepared, and transmission data was obtained with Illuminant D65 at an observer angle of 2°. This was processed using a color analysis device in the Grams/32 software to calculate Hunter L*a*b* values, and the results (L-b) by subtracting the b value from the L value were described in the table below.

4) Haze

A polyester resin specimen having a thickness of 6 mm was prepared, and the haze of the specimen was measured with a CM-3600A measuring instrument from Minolta in accordance with ASTM D1003-97.

The results are shown in Table 2 below.

TABLE 2

| Unit | r-BHET wt % | CHDM mol % | ISB mol % | IV dg/l | 6T Color L-b | 6T Haze |
|---|---|---|---|---|---|---|
| Example 1 | 30 | 8 | 2 | 0.70 | 93 | 1.5 |
| Example 2 | 75 | 5 | 2 | 0.95 | 90 | 2 |
| Example 3 | 89 | 4 | 0 | 0.80 | 87 | 3 |
| Example 4 | 14 | 5 | 0 | 0.85 | 91 | 2.5 |
| Example 5 | 50 | 30 | 0 | 0.70 | 90 | 2 |
| Example 6 | 1 | 20 | 15 | 0.80 | 88 | 0.8 |
| Example 7 | 69 | 8 | 3 | 0.95 | 87 | 1.8 |
| Example 8 | 75 | 5 | 2 | 1.00 | 88 | 2 |
| Comparative Example 1 | 31 | 5 | 1 | 0.70 | 85 | 10 |
| Comparative Example 2 | 7 | 50 | 1 | 0.75 | 82 | 3.5 |
| Comparative Example 3 | 92 | 0 | 4 | 0.85 | 86 | 25 |
| Comparative Example 4 | 16 | 8 | 1 | 0.70 | 82 | 3.8 |
| Comparative Example 5 | 16 | 30 | 0 | 0.60 | 80 | 4 |

As shown in Table 2, the polyester copolymers (Examples 1 to 8) prepared using bis-2-hydroxyethyl terephthalate purified according to the present disclosure had the excellent Color L-b value of 87 or more. On the other hand, the polyester copolymers prepared using bis-2-hydroxyethyl terephthalate prepared in Comparative Preparation Examples 1 to 3 (Comparative Examples 1, 2 and 4) and the polyester copolymers in which CHDM and ISB were not used in the polymerization (Comparative Examples 3 and 5) had the Color L-b value lower than the above value.

Accordingly, it was confirmed that when the bis-2-hydroxyethyl terephthalate purified by the purification method according to the present disclosure was used as a monomer of a polyester resin, the polyester had excellent color quality.

What is claimed is:

1. A method for preparation of a polyester copolymer comprising the steps of:
   1) Mixing bis-2-hydroxyethyl terephthalate and water (step 1);
   2) Adding activated carbon to the mixture of step 1 (step 2);
   3) Recovering bis-2-hydroxyethyl terephthalate from the mixture of step 2 (step 3);

4) Preparing an oligomer by an esterification reaction of an aqueous solution containing bis-2-hydroxyethyl terephthalate purified by step 3, a dicarboxylic acid or its derivative, and a diol containing ethylene glycol and a comonomer (step 4); and
5) preparing a polyester copolymer by a polycondensation reaction of the oligomer (step 5),
wherein a concentration of the aqueous solution containing bis-2-hydroxyethyl terephthalate is 25 to 99 wt %,
wherein the dicarboxylic acid or its derivative is terephthalic acid, dimethyl terephthalic acid, isophthalic acid, 2,6-naphthalenedicarboxylic acid, diphenyl dicarboxylic acid, 4,4'-stilbenedicarboxylic acid, 2,5-furandicarboxylic acid, or 2,5-thiophenedicarboxylic acid,
wherein the step 4 is performed at a pressure of 0.1 to 3.0 kg/cm$^2$ and a temperature of 200 to 300° C., and
wherein a haze measured with respect to a 6 mm-thick specimen of the prepared polyester copolymer is 3 or less.

2. The method of claim 1,
wherein the bis-2-hydroxyethyl terephthalate and water are mixed in a weight ratio of 1:100 to 99:100 in step 1.

3. The method of claim 1,
wherein a temperature of the water is 50 to 90° C. in step 1.

4. The method of claim 1,
wherein the activated carbon is added in an amount of 0.1 to 5.0 wt % based on a weight of the mixture of step 1 in step 2.

5. The method of claim 1,
wherein the step 3 is performed by filtering the mixture of step 2 to recover a filtrate.

6. The method of claim 5,
wherein the filtrate is cooled to 10 to 40° C. to recover bis-2-hydroxyethyl terephthalate crystals.

7. The method of claim 1,
wherein a temperature of the aqueous solution containing bis-2-hydroxyethyl terephthalate is 25 to 100° C.

8. The method of claim 1,
wherein the comonomer is cyclohexanedimethanol, isosorbide, or diethylene glycol.

9. The method of claim 1,
wherein the step 4 is performed for 2 hours to 10 hours.

10. A polyester copolymer prepared according to the method of claim 1.

11. The polyester copolymer of claim 10,
wherein the polyester copolymer comprises 1 to 90 wt % of the residue of bis-2-hydroxyethyl terephthalate.

12. The polyester copolymer of claim 10,
wherein the polyester copolymer has an intrinsic viscosity of 0.50 to 1.0 dl/g.

13. The polyester copolymer of claim 10,
wherein a value of (Hunter L value)–(Hunter b value) measured with respect to a 6 mm-thick specimen of the polyester copolymer is 87 or more.

14. A product comprising the polyester copolymer according to claim 10.

* * * * *